United States Patent [19]

Nichols

[11] Patent Number: 4,643,856
[45] Date of Patent: Feb. 17, 1987

[54] PROCESS OF MAKING GELLED CELLULOSE TRIACETATE PRODUCT

[75] Inventor: Larry D. Nichols, Arlington, Mass.

[73] Assignee: Moleculon, Inc., Cambridge, Mass.

[21] Appl. No.: 714,482

[22] Filed: Mar. 21, 1985

[51] Int. Cl.[4] .............................................. B29C 27/60
[52] U.S. Cl. ..................................... 264/41; 264/217; 264/218; 264/237; 264/348; 252/315.3
[58] Field of Search ................. 264/237, 348, 28, 218, 264/41, 217; 252/315.01, 315.1, 315.3, 315.4

[56] References Cited

U.S. PATENT DOCUMENTS

| | | | |
|---|---|---|---|
| 2,768,870 | 10/1956 | Drisch et al. | 264/218 |
| 2,999,760 | 9/1961 | Cacella et al. | 264/28 |
| 3,846,404 | 11/1974 | Nichols | 264/41 |
| 3,917,777 | 11/1975 | Asada et al. | 264/218 |
| 4,247,498 | 1/1981 | Castro | 264/28 |

*Primary Examiner*—James Lowe
*Assistant Examiner*—Hubert C. Lorin

[57] ABSTRACT

Gelled cellulose triacetate products are made by mixing with a solution of the cellulose triacetate an amount of miscible liquid nonsolvent agent insufficient to cause gelling, then cooling the mixture or evaporating the solvent to cause gelling.

12 Claims, No Drawings

PROCESS OF MAKING GELLED CELLULOSE TRIACETATE PRODUCT

This invention relates to a process of preparing a gelled cellulose triacetate product by mixing with a homogeneous solution of the cellulose triacetate a liquid gelling agent in an amount insufficient to cause gelling under the conditions of mixing, then cooling the mixture or selectively evaporating the solvent from the mixture to cause gelling.

It is known that solutions of cellulose triacetate (CTA) in certain solvents, particularly formic or acetic acid, can be converted into gelled membranes by forming the solution into a thin film and then immersing it in a miscible CTA non solvent, such as water or a light alcohol, at a temperature below 35° C. It is further known that such gelled CTA membranes possess utility both for membrane separation processes and for controlled delivery of medications into animals and humans. This utility arises from the unusual combination of advantageous properties displayed by gelled CTA membranes prepared in this manner: high liquid content, good mechanical strength, excellent liquid retentivity, optical clarity, controllable ultramicroscopic pore size, compatibility with most liquids and solutes, and the absence of surface barriers between the contained liquid and its immediate environment.

The foregoing method of manufacture, as fully described in U.S. Pat. 3,846,404, is effective and practical for products based on CTA solutions whose viscosity is sufficient to preserve the desired coating configuration from the moment of coating until the onset of gelation, despite the effects of gravity and immersion; and where contact between the substrate being coated and the necessary solvents and processing liquids poses no problems. These constraints do, however, impede many otherwise attractive product applications.

As one example, the optimization of membranes for transdermal delivery of medication frequently requires a gel layer a few millimeters thick containing more than 90% of internal liquid. Coating solutions capable of producing such high liquid content gels have a low viscosity. Applied in thick layers to a horizontal surface, they immediately spread unless confined at all edges, and any departure from the horizontal (as required for passage into a liquid immersion bath) leads to flow and loss of accurate thickness control. Moreover, the hydrodynamics of even low speed immersion causes rippling and surface distortion. These limitations are difficult to surmount simply by redesign of mechanical processing equipment; they stem from fundamental interactions between CTA solutions and any immersive coagulation system.

As a second example, enclosure or encapsulation of active materials within a gelled CTA coating is possible, in principle, by dip coating procedures of the prior art. However, during this process, the substances being enclosed are brought successively into contact with a variety of solvents and processing liquids: the original CTA solvent, the coagulating liquid, the final liquid desired within the gel coating, and any intermediate liquids needed to replace the coagulant by that final liquid. Each of these exposures provides opportunity for contamination, reaction and/or extractive loss of the ingredients being encapsulated. This severely limits the applicability of dip coating with CTA gels, which otherwise would be the method of choice for many small or irregular controlled dispensers.

A third example of limitations in the process of U.S. Pat. No. 3,846,404 is the difficulty in achieving extremely high optical clarity. It is known that clarity improves as the coagulation temperature is lowered, but the use of water as a coagulant restricts the temperature to values above 0° C. Light alcohols can be used as coagulants, and tend to give improved clarity, especially when even lower temperatures are employed; but use of alcohols in place of water significantly increases the cost and complexity of the production process. Clarity, which is especially important for applications involving optical measurements, becomes more difficult to achieve in absolute terms as thicker gel samples are produced, since the obscuring power of any haze increases rapidly with sample thickness. Excessively hazy gelled CTA products have inferior physical strength; clarity is a sensitive criterion of product quality even in the case of products in which optical clarity is not critical for their intended use.

In attempting to adapt the CTA gelation process of U.S. Pat. No. 3,846,404 to the need for thicker, clearer products having high liquid content and greater compatibility with encapsulating procedures, I have discovered methods for rapid gelation of certain CTA solutions without immersion in a non solvent liquid so as to replace the solvent with the non solvent. In particular, I have found that products similar in performance to those of U.S. Pat. No. 3,846,404 can be made by mixing with the solution of CTA a liquid gelling agent in an amount insufficient to cause gelling under the conditions of mixing, then either chilling the mixture or selectively evaporating the solvent from the mixture to cause gelling. This process enables close control over thickness and uniformity of thickness as well as improved clarity and freedom from haze of the gel product. Following gelation, the gel product may be immersed in any desired non solvent liquid, if desired, to remove any residual solvent or to replace the solvent or the liquid gelling agent with the non-solvent liquid. Chill gelling of CTA solutions greatly relaxes the constraints on production of dimensionally thick, high liquid content gel layers. Coating or casting of warm solution onto a cool surface almost immediately produces a gel layer which is virtually immune to flow or distortion even when subsequently inclined or immersed.

An unexpected benefit of the chill gelling procedure is that it yields CTA gel functionally similar to that of U.S. Pat. No. 3,846,404 but having substantially improved clarity even when water is employed as the immersion medium following gelation to rinse out or displace the original solvents.

The present invention features a process of preparing a clear gelled cellulose triacetate product which comprises providing a clear homogeneous liquid solution at a temperature of 20° to 60° C. comprising cellulose triacetate and a major proportion of a liquid solvent therefor, mixing with said solution while maintaining its temperature at 20° to 60° C., a clear liquid gelling agent miscible with said solvent, said gelling agent being a non solvent for cellulose triacetate and capable of causing said solution to gel, the amount of said gelling agent being limited to an amount insufficient to cause gelation at said maintained temperature and sufficient to cause gelation when said mixture is chilled by no more than 15° C., and chilling said mixture to cause gelation of said mixture. The invention also features a process of preparing a clear gelled cellulose triacetate product which comprises providing a clear homogeneous liquid solution comprising cellulose triacetate and a volatile organic liquid solvent therefor, mixing with said solution a clear liquid gelling agent which is a nonsolvent for cellulose triacetate and miscible with said volatile solvent and capable of causing said solution to gel, the amount of said gelling agent being limited to an amount insufficient to cause gelling of said mixture under the conditions of mixing, and exposing said mixture to the atmosphere to provide selective evaporation of said solvent from said mixture until gelation occurs.

The cellulose triacetate useful in the process of the present invention is any cellulose triacetate having an acetyl content greater than about 42 percent, and the cellulose triacetate gel products of the present invention possess generally the same properties and characteristics and are useful for the same purposes as those made by the process of U.S. Pat. No. 3,846,404 except that products made by the cooling or chilling process of the present invention exhibit markedly superior clarity and freedom from haze and are more readily formed into thick or complex configurations. The gel products made by the process of the present invention are generally uniform in composition and microstructure throughout their extent.

The solvents which can be used to form the homogeneous solution of cellulose triacetate in the initial stage of the present invention include liquids such as the acidic nonhydrolyzing solvents used in the process of the prior art, such as a water soluble organic acid having up to three carbon atoms, preferably formic, acetic, propionic, glycolic, monochloroacetic, or trifluoroacetic acid, and also include volatile organic solvents such as methylene chloride, chloroform, and the like. The concentration of cellulose triacetate in solution in such solvents may vary over a wide range, from about 1 to 25 percent by weight or even more. When acetic or formic acid is used as the solvent the concentration of CTA is preferably from 2 to 10% by weight, and the acid preferably contains no more than 13% water.

The liquid gelling agent, as stated above, may be any liquid which is a nonsolvent for the cellulose triacetate but which is miscible in the solvent and in the solution and capable of gelling of the solution when added in sufficient amount. It should be chemically inert to the cellulose triacetate and to the solvent. When the process involves selective evaporation of the solvent from the mixture of gelling agent, cellulose triacetate, and solvent, the gelling agent must have a lower rate of evaporation than the solvent under the conditions to be used to induce gelation. This difference in evaporation rate may be intrinsic to the two components, as in the case where the gelling agent has a lower vapor pressure than the solvent at the evaporation temperature, or it may be the result of controlled environmental conditions exterior to the gelling layer. That is, the external atmosphere may be maintained at or near saturation with respect to the vapor of the gelling agent, while being well below saturation with respect to the solvent vapor. Under such conditions a component of lower vapor pressure can be made to evaporate more rapidly than a component of higher vapor pressure.

The amount of liquid gelling agent added to the mixture must be less than the amount which causes gelation under the conditions of mixing, but preferably is at least 90% of the amount required to cause such gelation so as to minimize the extent of chilling or evaporation required. The mixture may be maintained at any desired temperature during mixing, from as low as 5° C. to as high as the boiling point of the solvent, but preferably is from about room temperature (20° C.) to about 85° C., better yet from 20° to 65° C. In some cases the rate of addition of the gelling agent and the efficiency of the stirring device used are important in order to avoid localized high concentration of gelling agent and consequent localized premature gelation. If the solvent is a water soluble organic acid as stated above, water alone may be used as the gelling agent if the mixture is to be gelled by cooling or chilling, or there may be used as the gelling agent isopropyl alcohol, ethylene glycol, propylene glycol, polyethylene glycol 400, tetrahydrofuran, hexylene glycol or the like; the polyethylene glycol 400 and hexylene glycol can also be used if the mixture is to be gelled by selective evaporation of the formic or acetic acid. When gelling is brought about by chilling, a solvent comprising a water-soluble organic acid, as above, is preferred, acetic acid being the solvent of choice, and water or isopropyl alcohol is desirable as the gelling agent, preferably isopropyl alcohol. If the solvent is an organic solvent such as methylene chloride or chloroform, there may be used polyethylene glycol 400 and hexylene glycol as the liquid gelling agent whether the gelling is caused by chilling or by evaporation of the volatile organic solvent. Esters and ethers are also suitable liquid gelling agents. It should be noted that some gelling agents may have a dual function, acting not only as the gelling agent but also as an active agent for delayed release from the gel product, as in the case of some pharmaceuticals or drugs, or insect repellants or controls. For example, the diethylene glycol ether of isostearyl alcohol is an effective and environmentally safe mosquito control material when distributed over bodies of water where mosquito larvae would otherwise mature. Its strong monolayer forming power and pronounced tendency to autoemulsify with water render the development of controlled release devices capable of maintaining anti-mosquito activity for a period of weeks a difficult task. Most dispensers either release their entire payload too rapidly, or draw water into their interior to produce an emulsion which fully or partially inhibits further release. It has been found that porous fibrous cylinders impregnated with the active liquid and coated with thin layer of CTA gel, itself containing the same active liquid, perform well as prolonged dispensers.

Dip coating of the porous liquid-filled cylinders into acetic acid solutions of CTA gives rise to difficult-to-remove contamination of the active liquid with acetic acid. Immersive gelation of such dip coated cylinders using water tends to produce a white emulsion within the coagulated coating and impair performance. Immersive coagulation with alternative CTA nonsolvents such as light alcohols tends to extract a prohibitive amount of the active liquid, and subsequent immersion of the completed encapsulated cylinders in diglycolisostearylether to restore full payload and leach out undesirable residues is extremely slow for cylinders of useful diameters of 5 mm or more.

In accordance with the present invention, a solution of CTA in methylene chloride or chloroform remains liquid when as much as 20% of the diglycol isostearylether is added with good mixing. When exposed to air or to additional diglycolisostearylether, films or coatings of such solutions gel in a matter of seconds. Dip coating on cylinders preloaded with the active ether involves both exposure to air and exposure to additional ether, and this process was found to produce highly effective mosquito control dispensers having a coating of CTA gel which contains the ether as active agent.

Gelation carried out in accordance with the present invention involves conversion from a true liquid form displaying viscous flow to a gel form in which no flow occurs until sufficient force is applied to cause permanent deformation or damage. The gelation normally occurs in a short period of time, being complete within a few seconds or minutes of its initiation.

In those cases where it is desired that the finished gel product incorporate an active agent such as a pharmaceutical, which it is not desired to use either as solvent or as gelling agent in the process, the gel product can be formed using any desired solvent and gelling agent, after which the gel product is immersed in the active agent or a solution thereof to exchange the latter for the residual solvent and gelling agent in the gel product. Similarly, when an acid is the solvent and isopropyl alcohol the gelling agent, the gel product can be immersed in water or an aqueous solution of an active agent such as a pharmaceutical in order to replace the residual acid and isopropyl alcohol with water or with the solution.

As an added and unexpected benefit, it was also found that a needle used to hold the cylinder during dip coating can be withdrawn during the brief period after the coating has begun to skin by evaporation but has not yet coagulated internally, to give a fully encapsulated product in which the needle hole is entirely sealed with gelled CTA.

The amount of liquid gelling agent required to cause gelling of solutions of CTA in various solvents under selected conditions can readily be determined by simple experiment. In practicing the invention it is usually desirable, although not essential, to mix into the CTA solution an amount of liquid gelling agent nearly sufficient, i.e. within about 10% by weight of the required amount, to cause gelling. If smaller amounts of gelling agent are employed, a greater extent of chilling or of evaporation of volatile solvent is required to bring about gelling. If larger amounts of gelling agent are mixed in the process becomes more difficult and expensive to control. The amount of gelling agent added, when chilling or cooling is to be employed to cause gelling of the mixture, is preferably no more than the amount which will result in a mixture requiring cooling by no more than 15° C., e.g. 5° C., to cause gelation; in some cases cooling by as much as 50° C. or more may be required for gelation. Such a temperature differential facilitates control of the process but may increase power requirements for heating or cooling. When selective evaporation of the solvent is employed to bring about gelation, it may be carried out at any desired temperature up to the boiling point of the solvent, but temperatures from 20° to 65° C. are preferred. If desired, the mixing of the gelling agent with the CTA solution may be carried out in a closed container to minimize premature heat loss and/or evaporation of solvent from the mixture, or other controls may be provided for this purpose. Excellent samples of gelled CTA materials containing 88% to 96% liquid have been prepared by blade coating a warm solution onto a cold surface, by pouring the solution into molds and cooling in situ, and by metered extrusion of the warm solution onto a cold roll. Samples of chill-gelled film 2.5 mm thick prepared by casting showed less absolute haze than films 0.5 mm thick prepared by the immersion process of the U.S. Pat. No. 3,846,404, even when the latter were prepared by immersive coagulation at 0° C. and the former were never exposed to temperatures below 25° C. during manufacture.

It should be understood that there are several interrelated parameters affecting gelation in the process of the present invention so that a change in one, such as temperature, may affect another, such as the amount of gelling agent or the specific identity of the gelling agent employed.

The following examples are intended to illustrate more clearly the nature of the invention without acting as a limitation upon its scope.

EXAMPLE 1

5.25 gm of cellulose triacetate (CTA) was dissolved in 44.75 gm of acetic acid (HAc) at 60° C. with good mixing maintained until the solution appeared homogeneous, a period of 12 hours. To that solution was then added, with good mixing, a solution of 41.63 gm of isopropyl alcohol (IPA) in 25.23 gm of HAc, prewarmed to 60° C. No evidence of polymer precipitation was observed, though prior experiments had shown that the addition of pure IPA at this stage would produce a CTA precipitate which was hard to redissolve. The final warm solution, protected against evaporation, was by weight 4.5% CTA, 35.6% IPA and 59.9% HAc. 9.8 gm of this warm solution was poured into a round, flat bottomed glass mold, 2 inches in diameter, at room temperature. Within 2 minutes a clear, nonfluid gel was observed to have formed. This was removed from the mold and rinsed with water until free from HAc and IPA. The resulting circular Poroplastic disk was 1.88 inches in diameter and 0.125 inches thick. It was found to contain 5.8 wt % CTA and 94.2% water. The increase in CT concentration between the initial solution and the final water containing gel, and the corresponding shrinkage, are entirely consistent with that observed during the immersive coagulation of conventional Poroplastic film as cited in the '404 patent.

EXAMPLE 2

CTA solutions prepared in the manner of Example 1 but having varying proportions of CTA, IPA and HAc, were slowly cooled in the cup of a Brookfield viscometer. The apparent viscosity increased slowly at first, then more rapdily, and finally dropped by a large factor as the spindle began to slip within the cylinder of gelled solution. Gel temperatures measured by this onset of slippage are listed below.

| wt % CTA | wt % IPA | wt % HAc | Gel Temperature |
|---|---|---|---|
| 4.5 | 31.4 | 64.1 | 28.1° C. |
| 4.5 | 34.2 | 61.3 | 37.6° C. |
| 4.5 | 35.7 | 59.8 | 38.7° C. |
| 4.5 | 37.1 | 58.4 | 38.8° C. |

EXAMPLE 3

Similar CTA solutions were poured into warm test tubes and sealed with rubber stoppers fitted with a thermocouple probe projecting into the warm liquid. As the liquids cooled, a sudden loss of fluidity was observed at a specific composition dependent temperature. These visual gel temperatures are tabulated below.

| wt % CTA | wt % IPA | wt % HAc | Gel Temperature |
|---|---|---|---|
| 4.5 | 31.4 | 64.1 | 29.1° C. |
| 4.5 | 34.2 | 61.3 | 38.4° C. |
| 4.5 | 35.7 | 59.8 | 39.5° C. |
| 4.5 | 37.1 | 58.4 | 42.0° C. |

EXAMPLE 4

A Poroplastic disk prepared as in Example 1 was immersed in PEG-400 for 24 hours, yielding a crystal clear sample of PEG-loaded gel.

EXAMPLE 5

A warm solution similar to that of Example 1 was poured into a standard casting box fitted with an adjustable knife, and drawn over a glass plate at a gap setting of 0.034". The resulting liquid film was observed to gel within 5 seconds, and was promptly immersed in water to extract residual HAc and IPA. The product was a Poroplastic film 0.019" thick analyzing 7.4 wt-% CTA.

EXAMPLE 6

The procedure of Example 5 was repeated with a 0.010" sheet of Tyvek nonwoven polyethylene fabric placed on the glass before the drawing operation. The gap setting was 0.044". This produced a Tyvek-backed Poroplastic film otherwise similar to the unbacked film of Example 5.

EXAMPLE 7

5.25 gm of CTA was dissolved in 44.75 gm of HAc at 60° C. in the manner of Example 1, and a solution of 53.4 gm of IPA in 71.6 gm of HAc was added in the manner explained. This solution (3.0 wt % CTA, 42.7% IPA and 54.3% HAc) was poured into a standard casting box, following Example 5, with a gap setting of 0.190". The resulting liquid film was observed to gel within 15 seconds and was promptly immersed in water to extract residual HAc and IPA. The Poroplastic film so produced was 0.100" thick and analyzed at 5.1 wt-% CTA.

EXAMPLE 8

The product of Example 5 was loaded with an antibiotic drug under conditions identical with those previously found to yield an effective antibiotic wound dressing from conventional, immersively coagulated Poroplastic film. Delivery rates of the drug into buffered isotonic saline were found to be identical, within experimental error, with those of the conventional product produced in accordance with the '404 patent.

EXAMPLE 9

Solutions prepared in the manner of Examples 1 and 2 were allowed to cool in small test tubes. The resulting gel bodies were accurate castings of the tube interior. Rinsed free from HAc and IPA with water, the resulting water impregnated gel bodies were faithful shrunken replicas of the original tubular mold.

EXAMPLE 10

The procedure of Example 9 was repeated, with the remaining ungelled liquid being poured out of the tubes before gelation was complete. This produced an accurate hollow casting of the tube interior, which was rinsed with water to yield a faithful shrunken replica with thin walls.

EXAMPLE 11

A solution of 5.25 gm of CTA was prepared in 44.75 gm of HAc as in Example 1. A prewarmed solution of 29.25 gm of water in 37.75 gm of HAc was then added with good mixing. The clear, homogeneous solution so obtained had a viscosity of 3200 cp, higher than that of a water-free solution containing the same concentration of CTA in pure HAc, 483 cp. This water-containing solution was found to convert on cooling to 35° C. to a highly transparent gel. After rinsing with water to remove residual acid, the resulting gel product was remarkably clear, in contrast to the highly hazy products obtained by coagulative gelation of CTA solutions in water warmer than 30° C., as cited in the U.S. Pat. No. 3,846,404.

EXAMPLE 12

Increasing the water content of the solution of Example 11 from 25% to 45% produced a gel even at temperatures as high as 70° C., while reducing the water content to 12.5% produced a solution which failed to gel at temperatures as low as 5° C.

EXAMPLE 13

80 gm of CTA was dissolved in 839 gm of methylene chloride by vigorous mixing for a period of 4 hours. To this clear, homogeneous solution was added a mixture of 120 gm of the diethylene glycol ether of isostearyl alcohol (DGIS) and 360 gm of methylene chloride. Again, good mixing was maintained to minimize any tendency for polymer precipitation during addition of the nonsolvent DGIS. The resulting colorless solution drained from a dipstick with no evidence of gel particles or other inhomogeneities. Poured into a tared aluminum dish, 0.968 gm of this volatile solution lost 0.830 gm of weight upon exposure to air for 1 hour. This weight loss of 85.7% agreed precisely with the methylene chloride weight percent calculated from the method of formulation. The nonvolatile residue was a clear film 0.042" thick. Extraction of the liquid component with four 50 ml portions of IPA, each conducted with swirling for 15 minutes, produced a crystal-clear specimen of Poroplastic gel impregnated with IPA. Drying in a vented air oven at 50° C. for 2 hours yielded a small, stiff residue of CTA weighing 0.0554 gm. Thus the CTA content of the original DGIS containing gel was 40.1%, again in good agreement with the formulation parameters.

EXAMPLE 14

The procedure of Example 13 was repeated using chloroform in place of methylene chloride. The appearance of the evaporatively gelled product was identical with that from methylene chloride, and the weight of nonvolatiles and insoluble CTA were again in agreement with the calculated values.

EXAMPLE 15

Small porous acetate cylinders of the type used as cigarette filters were saturated with DGIS and mounted axially on thin steel needles. Each cylinder was then immersed briefly, for about 1 second, in a solution prepared by the method of Example 13. Withdrawn from the coating solution into a methylene chloride saturated atmosphere, excess liquid was allowed to drain for about 5 seconds. Each sample was then withdrawn further into an environment substantially free from methylene chloride vapor. Within one or two seconds the surface of the liquid coating could be observed to skin over with gel. Forcible extraction of the needle through a narrow slotted fitting then collapsed the partially gelled meniscus surrounding the location of the needle, sealing the path of withdrawal. Lateral compression of such a coated reservoir by a 50 gm weight produced no visible expulsion of liquid over a 24 hour period.

EXAMPLE 16

A coated cylindrical reservoir prepared as in Example 15 was sliced lengthwise and its two half endcaps also sliced away. The remaining hemicylindrical coating of Poroplastic film was then delaminated from the reservoir, and the few adhering strands of acetate fiber removed by hand. This retrieved coating measured 0.004" thick. Extracted with IPA and dried as in Example 13, its CTA content was determined to be 22.3% by weight. Coagulation purely by evaporation would have led to a predicted CTA assay of 40.1%, while coagulation purely by solvent/nonsolvent exchange with the excess DGIS in the cylindrical reservoir would have led to a predicted value of 8.7%. The measured value lies between these extremes, corroborating that the actual gelation process was a combination of both mechanisms.

EXAMPLE 17

33.6 gm of CTA was dissolved in 638 gm of chloroform in the manner of Example 13, and a mixture of 4.5 gm of hexylene glycol with 19.8 gm of chloroform was added with good mixing. The resulting solution was colorless and free from observable inhomogeneities. A 15 cm piece of cellulose filter paper was moistened with hexylene glycol and placed on a glass plate. A small bead of the coating solution was placed on the glass adjacent to the paper, and a coating blade drawn across both the bead and the paper with a clearance of about 0.006". The chloroform was allowed to evaporate for 30 minutes, and the coated paper was then extracted with water to remove the glycol. Microscopic examination showed no perforations in the coating, whose thickness was measured to be slightly more than 0.001". Filtration of tap water through this coated paper showed it to be effective at removing particles of colloidal size. The distilled water filtration rate in an evacuated filter funnel was between 0.2 and 0.5 ml/cm$^2$/min. The calculated value for film of this thickness and composition using the data in the 3,876,404 patent is 0.2 ml/cm$^2$/min, close enough to corroborate the close similarity of the two methods of film preparation.

EXAMPLE 18

Two samples of film were prepared, one by immersive gelation of a solution of CTA in HAc using a cold water bath, and the other by chill gelling of a warm solution of CTA in a mixture of acetic acid and isopropyl alcohol. Both samples were 0.020" thick, and both were found to contain 8.0% CTA by weight after complete rinsing with water to remove all liquids other than water. Measurements of scattered light from a collimated beam passing through these samples showed that the immersively gelled film scattered 8% of the incident light, while film gelled by cooling scattered only 4% under identical test conditions. Thus the chill gelling process of the present invention produces a material which, in this case, has twice the optical clarity of the former, immersive product.

EXAMPLE 19

A stock solution of 13 wt. % CTA in trifluoroacetic acid (TFA) was prepared. A mixture of 15.6 g of IPA and 7.1 g TFA was prepared as a gelling agent. This mixture was added to 12 g of the 13% solution of CTA in TFA at room temperature with blade stirring. This formed a homogeneous solution which, when poured on an ice cold plate, formed a stable gel in several seconds. Two such gels were produced, and one was submerged in water while the other was submerged in IPA. The water immersed product was bubbly and nonuniform, while the IPA immersed product was without bubbles and appeared quite uniform. When the IPA-immersed product wasd subsequently placed in a water bath for exchange, no noticeable dimensional changes in the gel product occurred.

EXAMPLE 20

10 g of the 13% CTA/TFA solution of Example 19 was combined with 42.1 ml TFA and 11.7 ml hexylene glycol. This corresponds to a 1:9 ratio of CTA: glycol with 80 vol. % TFA in the mixture. When a layer of this formulation was spread on glass and the TFA evaporated, a thin CTA film is left impregnated with glycol.

EXAMPLE 21

30 parts by weight of CTA were dissolved in 70 parts of commercial formic acid known to contain 10% water. The resulting solution was warmed to 60° C., and to it was added a 60° C. solution made from 65.4 ml of IPA and 17.7 ml of the same formic acid. After mild stirring a clear homogeneous mixture was obtained containing 2.25% CTA, 47.75% formic acid, and 50% IPA. Poured onto a glass plate precooled to near 0° C., a portion of this solution gelled in less than 5 seconds to a clear, non-liquid product which, upon rinsing with sufficient water to remove residual acid and alcohol proved to be a CTA gel containing 8% CTA by weight and having good final clarity. Subsequent experiments showed that the maximum temperature of the plate capable of causing prompt gelation of this mixture was 22°-24° C.

What is claimed is:

1. A process of preparing a clear gelled cellulose triacetate product which comprises
   providing a clear homogeneous liquid solution at a temperature of 20° to 60° C. comprising cellulose triacetate having an acetyl content greater than about 42%, and a major proportion of a liquid solvent therefor,
   mixing with said solution while maintaining its temperature at 20° to 60° C., a clear liquid gelling agent miscible with said solvent, said gelling agent being a nonsolvent for said cellulose triacetate and capable of causing said solution to gel,
   the amount of said gelling agent being limited to an amount insufficient to cause gelation at said maintained temperature but sufficient to cause gelation when said mixture is chilled, and
   chilling said mixture to gel said mixture.

2. A process as claimed in claim 1 in which said mixed solution is shaped to a product configuration prior to said chilling step.

3. A process as claimed in claim 1 in which said solvent comprises a water-soluble organic acid having 1 to 3 carbon atoms and said gelling agent is water or isopropyl alcohol.

4. A process as claimed in claim 1 in which said solvent comprises acetic acid and said gelling agent comprises isopropyl alcohol.

5. A process as claimed in claim 1 including the additional step of contacting said gel with a liquid which is both a nonsolvent for the cellulose triacetate and miscible with the solvent and gelling agent present for a period of time so as to replace substantially all of said solvent and gelling agent with said nonsolvent.

6. A process as claimed in claim 5 in which said solvent is acetic acid, said gelling agent is isopropyl alcohol, and said miscible nonsolvent is water.

7. A process of preparing a clear gelled cellulose triacetate product which comprises
providing a clear homogeneous liquid solution comprising cellulose triacetate having an acetyl content greater than about 42%, and a volatile organic liquid solvent therefor
mixing with said solution a clear liquid gelling agent which is a nonsolvent for said cellulose triacetate and miscible with said volatile solvent and capable of causing said solution to gel,
the amount of said gelling agent being limited to an amount insufficient to cause gelling of said mixture under the conditions of mixing, and
exposing said mixture to an atmosphere to provide selective evaporation of said solvent from said mixture until gelation occurs.

8. A process as claimed in claim 7 in which said mixed solution is shaped to a product configuration prior to said evaporation step.

9. A process as claimed in claim 7 in which said volatile solvent is methylene chloride or chloroform.

10. A process as claimed in claim 7 in which said mixture is maintained at a temperature from 20° to 65° C. during said evaporation step.

11. A process as claimed in claim 7 in which said solvent is a water-miscible organic acid having 1 to 3 carbon atoms and said gelling agent is water or isopropyl alcohol.

12. A process as claimed in claim 7 in which said solvent comprises acetic acid and said gelling agent comprises isopropyl alcohol.

* * * * *